(12) United States Patent
Rawlins et al.

(10) Patent No.: US 7,585,312 B2
(45) Date of Patent: Sep. 8, 2009

(54) SPINAL STABILIZATION APPARATUS AND METHOD

(75) Inventors: Bernard A. Rawlins, Alpine, NJ (US); Alan Rezach, Atoka, TN (US); David A. Warmbold, Collierville, TN (US); Keith Miller, Germantown, TN (US); Marco Capote, Memphis, TN (US); Douglas Baker, Collierville, TN (US); Anthony Dickinson, Millington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 497 days.

(21) Appl. No.: 11/118,995

(22) Filed: Apr. 29, 2005

(65) Prior Publication Data

US 2006/0247628 A1    Nov. 2, 2006

(51) Int. Cl.
*A61B 17/70* (2006.01)
(52) U.S. Cl. .................................................. 606/246
(58) Field of Classification Search ............. 606/54–59, 606/61
See application file for complete search history.

(56) References Cited

U.S. PATENT DOCUMENTS

| | | | |
|---|---|---|---|
| 1,873,559 A * | 8/1932 | Dibner | 403/396 |
| 2,940,783 A * | 6/1960 | Engelhardt | 403/389 |
| 4,611,581 A | 9/1986 | Steffee | |
| 4,648,388 A | 3/1987 | Steffee | |
| 4,655,199 A | 4/1987 | Steffee | |
| 5,002,542 A | 3/1991 | Frigg | |
| 5,127,912 A | 7/1992 | Ray et al. | |
| 5,129,844 A * | 7/1992 | Goto et al. | 439/778 |
| 5,129,900 A | 7/1992 | Asher et al. | |
| 5,290,288 A | 3/1994 | Vignaud et al. | |
| 5,476,463 A | 12/1995 | Boachie-Adjei et al. | |
| 5,662,651 A * | 9/1997 | Tornier et al. | 606/60 |
| 5,810,816 A | 9/1998 | Roussouly et al. | |
| 5,928,233 A * | 7/1999 | Apfelbaum et al. | 606/61 |
| 5,938,663 A | 8/1999 | Petreto | |
| 5,976,135 A * | 11/1999 | Sherman et al. | 606/61 |
| 6,030,388 A | 2/2000 | Yoshimi et al. | |

(Continued)

FOREIGN PATENT DOCUMENTS

DE    20 2004 018037 U1    1/2005

(Continued)

OTHER PUBLICATIONS

Written Opinion of the International Searching Authority in connection with International Application No. PCT/US2006/016534, filed Jan. 5, 2006.

(Continued)

*Primary Examiner*—Thomas C Barrett
*Assistant Examiner*—Nicholas Woodall (57) ABSTRACT

A spinal stabilization apparatus and method according to which a fastener is engaged with a vertebra of a spinal system. The fastener is connected to a rod and the direction of extension of at least a portion of the rod in a coronal plane may be selectively adjusted.

19 Claims, 6 Drawing Sheets

U.S. PATENT DOCUMENTS

| | | | |
|---|---|---|---|
| 6,176,861 B1 | 1/2001 | Bernstein et al. | |
| 6,183,473 B1* | 2/2001 | Ashman | 606/61 |
| 6,248,107 B1 | 6/2001 | Foley et al. | |
| 6,520,990 B1 | 2/2003 | Ray | |
| 6,572,618 B1* | 6/2003 | Morrison | 606/61 |
| 7,044,426 B1* | 5/2006 | Allmon et al. | 248/500 |
| 7,232,441 B2* | 6/2007 | Altarac et al. | 606/61 |
| 2002/0049446 A1* | 4/2002 | Harkey et al. | 606/70 |
| 2004/0210216 A1* | 10/2004 | Farris et al. | 606/61 |

FOREIGN PATENT DOCUMENTS

| | | |
|---|---|---|
| JP | 09 327467 | 12/1997 |

OTHER PUBLICATIONS

International Search Report in connection with International Application No. PCT/US2006/016534, filed Jan. 5, 2006.

Steve Heim, M.D., Medtronic Sofamor Danek DYNALOK Classic Spinal System Surgical Technique, Year 2000, USA.

* cited by examiner

SPINAL STABILIZATION APPARATUS AND METHOD

BACKGROUND

The present invention relates in general to spinal systems and in particular to a spinal stabilization apparatus and method.

To stabilize a spinal system including a spinal column, the extent of displacement between adjacent vertebrae in the spinal column may be reduced, and/or each pair of adjacent vertebrae may be maintained in a desired spatial relationship.

In some cases, rods may be provided that are adapted to extend within the vicinity of the spinal system, and connectors may be provided that connect one or more of the rods to one or more of the vertebrae in the spinal system. The rods and connectors may assist in providing immobilization and/or stabilization to the spinal system, and/or may serve as an adjunct to fusion of one or more portions of the spinal system. An example of a system for reducing displacement of a vertebra, in which a rod is employed, is disclosed in U.S. Pat. No. 6,248,107 to Foley et al., the disclosure of which is incorporated by reference.

For spinal stabilization systems that include one or more rods, the ability to selectively adjust the direction of extension of at least a portion of one of the rods in a coronal plane may be desired and/or required, among other desires and/or requirements. As used herein, it is understood that the term "coronal plane" includes any plane of section in the anatomical position that generally passes vertically through the human body and is generally perpendicular to both the median (or sagittal) plane and the horizontal (or axial or transverse) plane, generally dividing the human body into anterior and posterior sections, and further includes any plane of section in the anatomical position that generally passes vertically through the human body, is generally perpendicular to the horizontal (or axial or transverse) plane, and is generally angularly oriented from the median (or sagittal) plane at an angle of orientation ranging from greater than zero degrees up to and including ninety degrees.

SUMMARY OF THE INVENTION

According to one aspect of the present invention, an apparatus for stabilizing a spinal system is provided that includes a plate member adapted to be coupled to a vertebra of the spinal system, and means coupled to the plate member for selectively adjusting the direction of extension of at least a portion of a rod in a first coronal plane, wherein the at least a portion of the rod engages the adjusting means when the rod extends within the vicinity of the spinal system.

According to another aspect of the present invention, a method of stabilizing a spinal system is provided that includes engaging a fastener with a vertebra of the spinal system, connecting the fastener to a rod extending within the vicinity of the spinal system, and selectively adjusting the direction of extension of at least a portion of the rod in a first coronal plane.

DETAILED DESCRIPTION

Figure 1:
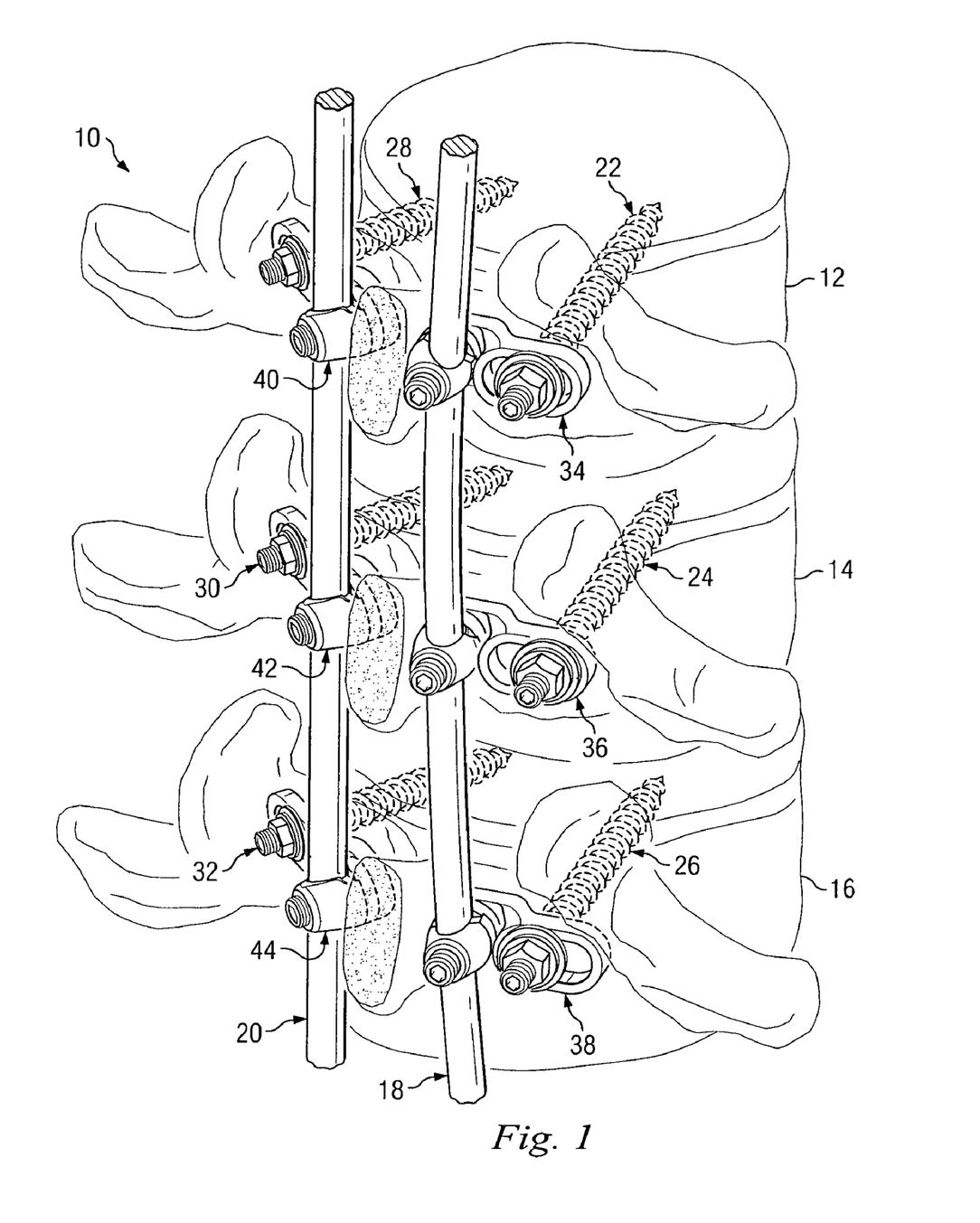
FIG. 1 is a perspective view of a spinal system including a plurality of connectors.

Referring to FIG. 1, a spinal system is generally referred to by the reference numeral 10 and includes vertebrae 12, 14 and 16. It is understood that the spinal system 10 includes a human spinal column composed of various types of vertebrae, of which the vertebrae 12, 14 and 16 are a part, and ligaments and/or other natural and/or artificial structures connected to and/or extending between one or more of the vertebrae. Rods 18 and 20 extend within the vicinity of the spinal system 10 in a spaced relation. Fasteners, in the form of pedicle screws 22, 24 and 26, are threadably engaged with and extend from the right-side pedicles of the vertebrae 12, 14 and 16, respectively. In a like manner, fasteners in the form of pedicle screws 28, 30 and 32 are threadably engaged with and extend from the left-side pedicles of the vertebrae 12, 14 and 16.

Connectors 34, 36 and 38 are engaged with the pedicle screws 22, 24 and 26, respectively, and are coupled to the rod 18, thereby connecting the screws 22, 24 and 26 to the rod 18. Likewise, connectors 40, 42 and 44 are engaged with the pedicle screws 28, 30 and 32, respectively, and are coupled to the rod 20, thereby connecting the screws 28, 30 and 32 to the rod 20.

Figure 2:
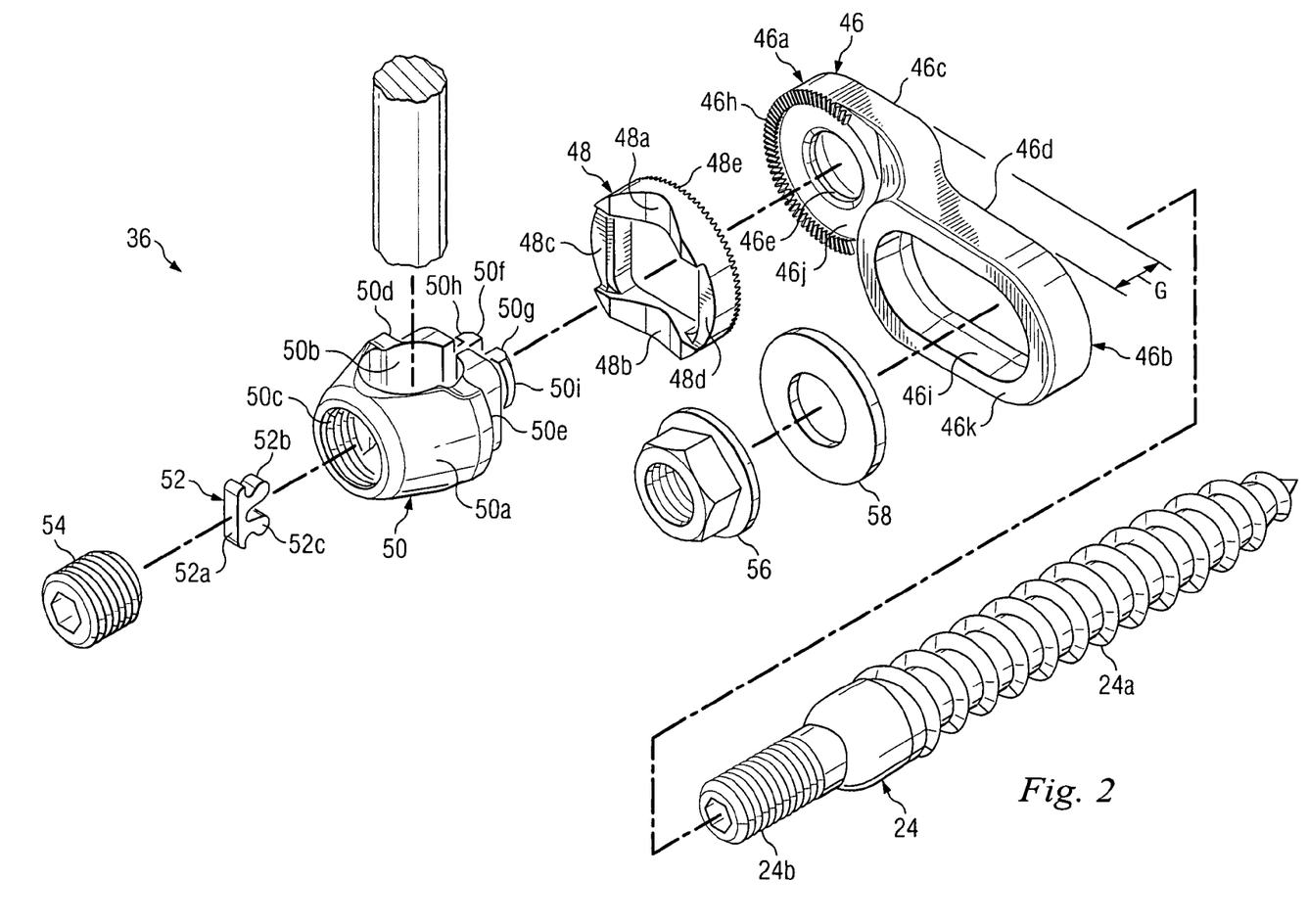
FIG. 2 is an exploded perspective view of a connector according to an embodiment of the present invention and shown in FIG. 1.
Figure 3:
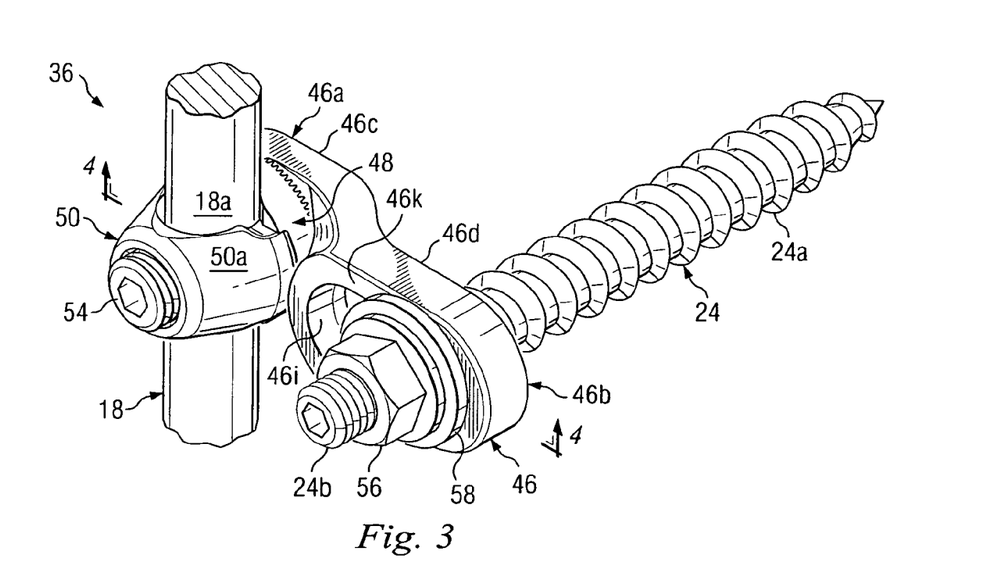
FIG. 3 is an unexploded perspective view of the connector of FIG. 2.
Figure 4:
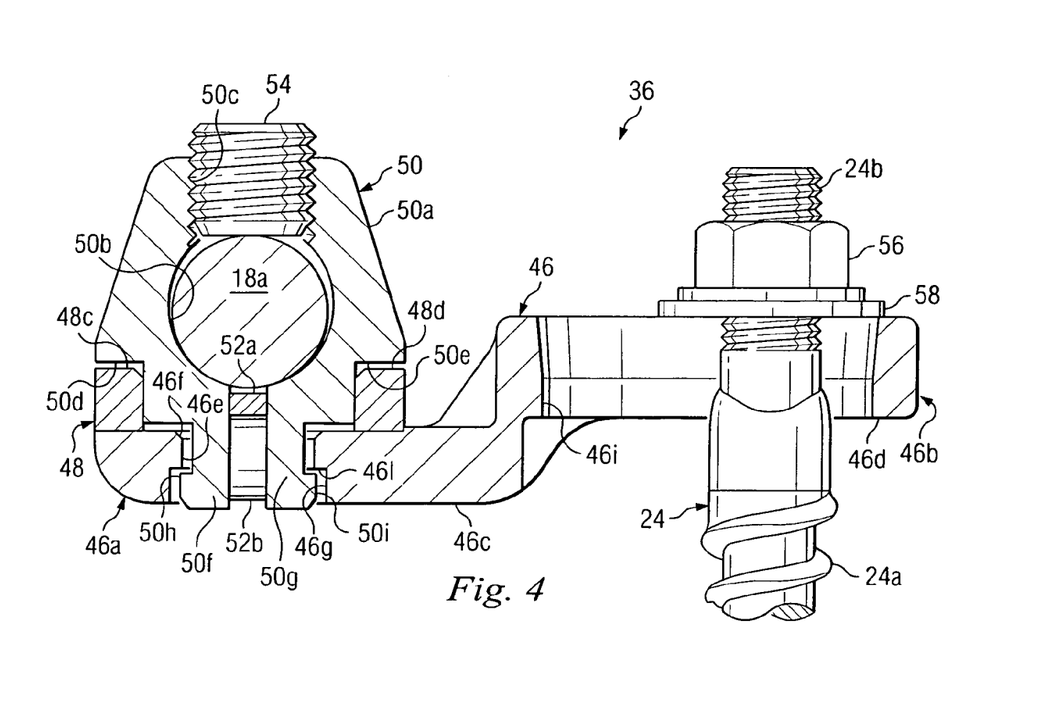
FIG. 4 is a sectional view of the connector of FIG. 2 taken along line 4-4.

Referring to FIGS. 2 through 4, the connector 36 includes a plate member 46 having an end portion 46a and an end portion 46b extending therefrom, with the end portions 46a and 46b defining planar surfaces 46c and 46d, respectively, the edges of which are shown in FIGS. 2-4. The planar surfaces 46c and 46d are spaced from each other by a distance G in an offset direction that is perpendicular to the planar surfaces 46c and 46d.

A countersunk bore 46e is formed through the end portion 46a, and includes a countersunk portion 46f and an increased-diameter portion 46g below the countersunk portion 46f (shown in FIG. 4). A plurality of teeth 46h is formed in a surface of the end portion 46a opposing the planar surface 46c, with the plurality of teeth 46h partially circumferentially extending about the countersunk bore 46e. A through-opening such as a slot 46i is formed in the end portion 46b. The end portions 46a and 46b further define planar surfaces 46j and 46k, respectively, and the increased-diameter portion 46g of the bore 46e defines a surface 46l (shown in FIG. 4).

A washer 48 includes a pair of opposing generally V-shaped cut-outs 48a and 48b and a pair of opposing grooves 48c and 48d. A plurality of teeth 48e is formed in a surface of the washer 48 opposing the cut-outs 48a and 48b and the grooves 48c and 48d.

A housing member 50 includes a collar portion 50a having a through-opening 50b extending therethrough, and a bore 50c extending into the through-opening 50b, the bore 50c having an internal threaded connection. Undercuts 50d and 50e are formed in the collar portion 50a, and a pair of generally parallel-spaced arms 50f and 50g extend from the collar portion 50a, the arms 50f and 50g having increased-size distal end portions 50h and 50i, respectively.

A clip member 52 includes a vertically-extending portion 52a and pair of spaced legs 52b and 52c extending therefrom, with each leg 52b and 52c extending in a direction away from the other leg. The legs 52b and 52c of the clip member 52 are adapted to flex towards and away from each under conditions to be described. The connector 34 further includes a fastener such as a set screw 54, a nut 56 and a washer 58, and the pedicle screw 24 includes a threaded portion 24a adapted to threadably engage the vertebra 14, and a threaded portion 24b adapted to extend through the washer 58 and threadably engage the nut 56.

To place the connector 36 is in its assembled condition, as shown in FIGS. 3 and 4, the arms 50f and 50g of the housing member 50 are inserted through the washer 48 until the vertically-extending surfaces of the collar portion 50a defined by the undercuts 50d and 50e engage and are seated in the grooves 48c and 48d, respectively, of the washer 48. Before, during or after the engagement between the housing member 50 and the washer 48, it is understood that an adhesive such as, for example, a silicone adhesive may be applied to portions of the housing member 50 and/or to portions of the washer 48 to provide a more generally permanent engagement between the housing member 50 and the washer 48. For example, a silicone adhesive may be applied to the surfaces of the washer 48 defined by the grooves 48c and 48d.

The arms 50f and 50g of the housing member 50 are then inserted into the bore 46e of the plate member 46. As the arms 50f and 50g are inserted into the bore 46e, the increased-size distal end portions 50h and 50i engage the countersunk portion 46f, thereby causing at least the distal end portions 50h and 50i of the arms 50f and 50g, respectively, to flex towards each other so that the arms 50f and 50g may be inserted through the bore 46e.

Upon entry into the increased-diameter portion 46g of the bore 46e, the distal end portions 50h and 50i move back to their initial positions relative to one another, thereby forming a snap fit and coupling the housing member 50 to the plate member 46, with the washer 48 disposed therebetween. It is understood that the housing member 50 and the washer 48 may have a limited degree of freedom of translation in an up-and-down direction, relative to the plate member 46 and as viewed in FIG. 4.

The clip member 52 is inserted into the bore 46e, causing the legs 52b and 52c to flex towards each other. Insertion of the clip member 52 is continued until the portion 52a engages the planar surface 46j of the plate member 46. At this point, the legs 52b and 52c are disposed between the arms 50e and 50f of the housing member 50, and at least the distal ends of the legs 52b and 52c have flexed away from each other and are disposed in the increased-diameter portion 46g of the bore 46e, engaging the surface 46l of the plate member 46 defined by the increased-diameter portion 46g. Due to the opposing directions of extension of the legs 52b and 52c, the legs 52b and 52c are biased away from each other when disposed between the arms 50e and 50f and engaging the surface 46l, thereby securing the clip member 52 to the plate member 46.

As a result of the disposal of the legs 52b and 52c of the clip member 52 between the arms 50f and 50g of the housing member 50, the arms 50e and 50f are prevented from moving towards each other so as to enable the increased-size portions 50h and 50i of the arms 50f and 50g, respectively, to pass through the bore 46e. Thus, the clip member 52 retains the housing member 50 to the plate member 46, preventing any decoupling therebetween.

At this point, due in part to the limited degree of freedom of translation in the up-and-down direction as viewed in FIG. 4, the housing member 50 and the washer 48 are free to rotate in place, up to 360 degrees and relative to the plate member 46, about an imaginary axis that is substantially coaxial with the center axis of the bore 46e. As the housing member 50 and the washer 48 rotate, the direction of extension of the through-opening 50b is selectively adjusted. Since the center axis of the bore 46e, and therefore the substantially coaxial imaginary axis about which the housing member 50 and the washer 48 rotate, is perpendicular to the planar surfaces 46c, 46d, 46j and 46k, it is understood that the direction of extension of the through-opening 50b is selectively adjusted in a plane that is either substantially coplanar or parallel with the planar surfaces 46c, 46d, 46j and/or 46k.

To lock the direction of extension of the through-opening 50b at a desired position, the housing member 50 and the washer 48 may be rotated to adjust the direction of extension of the through-opening 50b to the desired position, and the washer 48 may be moved towards the plate member 46 so that the plurality of teeth 48e of the washer 48 meshes with the plurality of teeth 46h of the plate member. The meshing of the pluralities of teeth 48e and 46h prevents further rotation of the washer 48 relative to the plate member 46 and, correspondingly, prevents the further rotation of the housing member 50 due to the extension of the collar portion 50a into the grooves 48c and 48d of the washer 48. Thus, the direction of extension of the through-opening 50b is locked.

It is understood that the direction of extension of the through-opening 50b may be selectively adjusted and locked in predetermined angular increments, with each predetermined angular increment corresponding to the spacing between each pair of adjacent teeth in the pluralities of teeth 48e and 46h. For example, the peak-to-peak or valley-to-valley spacing between each pair of adjacent teeth in the pluralities of teeth 48e and 46h may be 6 degrees. Thus, the direction of extension of the through-opening 50b may be selectively adjusted and locked in 6-degree angular increments.

After selectively adjusting the direction of extension of the through-opening 50b, and also locking the direction of extension of the through-opening 50b if desired, the rod 18 is inserted through the through-opening 50b of the housing member 50 so that a portion 18a of the rod 18 engages the washer 48 and is seated in the cut-outs 48a and 48b. The set screw 54 is threadably engaged with the bore 50c so that the set screw 54 extends through the bore 50c and into the through-opening 50b, contacting the rod portion 18a. Further threaded engagement between the set screw 54 and the bore 50c causes the rod portion 18a to bear against the surfaces of the washer 48 defined by the cut-outs 48a and 48b, thereby substantially preventing relative movement between the rod 18 and the housing member 50.

Since the rod 18 is inserted through the through-opening 50b so that the rod portion 18a engages the washer 48, it is understood that, by selectively adjusting the direction of extension of the through-opening 50b in the manner described above, the direction of extension of the rod portion 18a is also selectively adjusted in a plane that is either substantially coplanar or parallel with one or more of the planar surfaces 46c, 46d, 46j and/or 46k. For the same reasons, it is further understood that, by selectively adjusting the direction of extension of the through-opening 50b in predetermined angular increments in the manner described above, the direction of extension of the rod portion 18*a* is also selectively adjusted in predetermined angular increments. And it is further understood that, by locking the direction of extension of the through-opening 50*b* in the manner described above, the direction of extension of the rod portion 18*a* is also locked.

The connectors 34, 38, 40, 42 and 44 are substantially identical to the connector 36 and therefore will not be described in detail. The placement of each of the connectors 34, 38, 40, 42 and 44 in their assembled conditions is substantially identical to the above-described placement of the connector 36 in its assembled condition and therefore these placements will not be described in detail.

The engagement between the rod 18 and the connectors 34 and 38, and the engagement between the rod 20 and the connectors 40, 42 and 44, are substantially identical to the above-described engagement of the rod 18 with the connector 36 and therefore these engagements will not be described in detail. It is understood, however, that the locked directions of extension of the portions of the rod 18 engaged with the connectors 34 and 38 may differ from each other, and from the locked direction of extension of the rod portion 18*a* engaged with the connector 36. Similarly, it is understood that the locked directions of extension of the portions of the rod 20 engaged with the connectors 40, 42 and 44 may differ from each other.

Referring back to FIG. 1 with continuing reference to FIGS. 2-4, the threaded portion 24*a* of the pedicle screw 24 is threadably engaged with the vertebra 14 so that the pedicle screw 24 extends from the vertebra 14 in a generally anterior-to-posterior direction away from the spinal system 10. Similarly, the pedicle screws 22 and 28 are threadably engaged with and extend from the vertebra 12, the pedicle screw 30 is threadably engaged with and extends from the vertebra 14, and the pedicle screws 26 and 32 are threadably engaged with and extend from the vertebra 16.

After engagement with the rod 18 in the above-described manner, the connectors 34, 36 and 38 are positioned so that the pedicle screw 24 extends through the slot 46*i* of the connector 36, and the pedicle screws 22 and 26 extend through the corresponding slots 46*i* of the connectors 34 and 38, respectively. As a result, the rod 18 extends within the vicinity of the spinal system 10. At this point, the washer 58 and the nut 56 may be positioned so that the threaded portion 24*b* of the pedicle screw 24 extends through the washer 58 and threadably engages the nut 56. It is understood that the engagements between the connector 34 and the pedicle screw 22, and between the connector 38 and the pedicle screw 26, are substantially similar to the engagement between the connector 36 and the pedicle screw 24 and therefore will not be described in detail.

It is understood that the slot 46*i* of the connector 36 enables the connector 36 to translate in a coronal plane, relative to the pedicle screw 24 and the vertebra 14, and that the corresponding slots 46*i* of the connectors 34 and 38 enable the connectors 34 and 38 to translate in coronal planes relative to the pedicle screws 22 and 26, respectively, and the vertebrae 12 and 16, respectively. As used herein, it is understood that the term "coronal plane" includes any plane of section in the anatomical position that generally passes vertically through the human body and is generally perpendicular to both the median (or sagittal) plane and the horizontal (or axial or transverse) plane, generally dividing the human body into anterior and posterior sections, and further includes any plane of section in the anatomical position that generally passes vertically through the human body, is generally perpendicular to the horizontal (or axial or transverse) plane, and is generally angularly oriented from the median (or sagittal) plane at an angle of orientation ranging from greater than zero degrees up to and including ninety degrees.

As shown in FIG. 1, the connector 36 is translated in a coronal plane to the left and the connector 38 is translated in another coronal plane to the right, and it is understood that the coronal planes may be substantially coplanar. It is understood that the connectors 34, 36 and/or 38 may be translated to avoid and/or clear features of the vertebrae 12, 14 and/or 16, respectively, and/or other natural and/or artificial structures connected thereto and/or extending therebetween.

After the connector 36 is positioned as desired and/or necessary, the nut 56 is further threadably engaged with the threaded portion 24*b* of the pedicle screw 24 and is thereby tightened so that the any relative translation and/or movement, between the connector 36 and the vertebra 14, is prevented and the planar surface 46*d* is engaged with the vertebra 14, thereby coupling the connector 36 to the vertebra 14. Due to the offset spacing G between the planar surfaces 46*c* and 46*d*, the degree of projection of the rod portion 18*a* in a generally anterior-to-posterior direction away from the spinal system 10 is reduced. Similarly, the corresponding nuts 56 of the connectors 34 and 38 are also tightened, thereby coupling the connectors 34 and 38 to the vertebrae 12 and 16, respectively.

As shown in FIG. 1, each of the planar surfaces 46*c*, 46*d*, 46*j* and 46*k* of the plate member 46 of the connector 36 generally lies in a coronal plane within the vicinity of the spinal system 10. Since, as described above, the direction of extension of the rod portion 18*a* is able to be selectively adjusted in a plane that is either parallel or substantially coplanar with one or more of the planar surfaces 46*c*, 46*d*, 46*j* and/or 46*k*, it follows that the direction of extension of the rod portion 18*a* is able to be selectively adjusted in a coronal plane within the vicinity of the spinal system 10.

As further shown in FIG. 1, the housing member 50 of the connector 36 has been rotated, relative to the plate member 46, so that the rod portion 18*a* engaged with the housing member 50 of the connector 36 extends in a generally vertical direction in a coronal plane within the vicinity of the spinal system 10. Dissimilarly, the corresponding housing members 50 of the connectors 34 and 38 have been rotated to the right and left, respectively. Thus, the portions of the rod 18 engaged with the connectors 34 and 38 extend in coronal planes within the vicinity of the spinal system 10, but in directions that vary from each other and the rod portion 18*a*.

Instead of engaging the rod 18 with the connectors 34, 36 and 38, and then coupling the connectors 34, 36 and 38 to the vertebrae 12, 14 and 16, respectively, it is understood that the connectors 34, 36 and 38 may first be coupled to the vertebrae 12, 14 and 16, respectively, and the rod 18 may then be fed through the through-openings 50*b* of the connectors 34, 36 and 38. It is further understood that, prior to feeding the rod 18, the directions of extension of the through-openings 50*b* of the connectors 34, 36 and 38 may be locked.

It is understood that the directions of extension of different portions of the rod 18 in one or more coronal planes within the vicinity of the spinal system 10 may each be selectively adjusted to form a wide variety of arrangement for a wide variety of reasons such as, for example, in order to avoid and/or clear features of the vertebrae 12, 14 and/or 16, and/or other natural and/or artificial structures connected to one or more of the vertebrae, extending between two or more of the vertebrae, and/or connected to the rod 18 and/or the connectors 34, 36 and/or 38.

It is understood that the implementation and arrangement of the rod 20, and the connectors 40, 42 and 44 engaged therewith, within the vicinity of the spinal system 10 is substantially identical to the above-described implementation and arrangement of the rod 18, and the connectors 34, 36 and 38 engaged therewith, and therefore will not be described in detail.

In operation, the rods 18 and 20, and the connectors 34, 36, 38, 40, 42 and 44, assist in providing immobilization and/or stabilization to the spinal system 10, and/or may serve as an adjunct to fusion of one or more portions of the spinal system 10. It is understood that the extent of displacement between the vertebrae 12 and 14, and/or the vertebrae 14 and 16, and/or other vertebra in the spinal column of the spinal system 10 may be reduced, and/or one or more pairs of adjacent vertebrae may be maintained in a desired spatial relationship.

Figure 5:
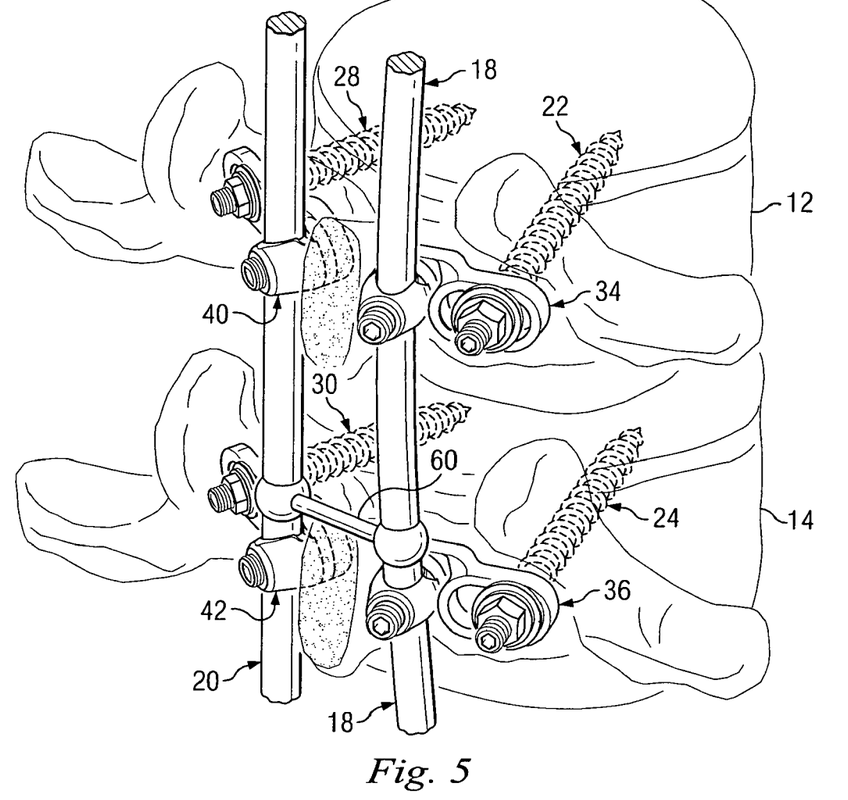
FIG. 5 is a perspective view of the spinal system but depicting another operational mode of the connector of FIG. 2.

Referring to FIG. 5, with continuing reference to FIGS. 1-4, a crosslink 60 is connected to and extends between the rods 18 and 20. It is understood that the direction of extension of the rod portion 18a may be selectively adjusted in a coronal plane within the vicinity of the spinal system 10 to assist in the crosslink 60 avoiding and/or clearing one or more features of the vertebra 14, and/or other natural and/or artificial structures connected to one or more of the vertebra in the spinal system 10, extending between two or more of the vertebrae in the spinal system 10, and/or connected to the rods 18 and 20 and/or the connectors 34, 36, 38, 40, 42 and/or 44.

Figure 6:
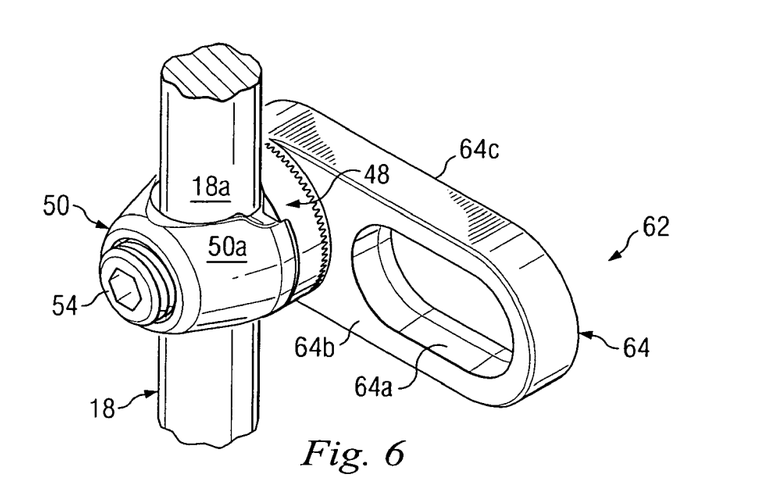
FIG. 6 is a perspective view of a connector according to another embodiment of the present invention.

Referring to FIG. 6, another embodiment of a connector is generally referred to by the reference numeral 62, and is similar to that of the connector 36 of the embodiment of FIGS. 1-5 and contains parts of the embodiment of FIGS. 1-5 that are given the same reference numerals. In the embodiment of FIG. 6, the connector 62 includes a plate member 64 having an opening such as a slot 64a formed therethrough, and defining a planar surface 64b and a planar surface 64c, the edge of which is shown in FIG. 6.

The placement of the connector 62 in its assembled condition is substantially identical to the placement of the connector 36 in its assembled condition, and therefore the assembly of the connector 62 will not be described in detail. It is understood that the housing member 50 is coupled to the plate member 64, with the washer 48 disposed therebetween, in the same manner as the housing member 50 is coupled to the plate member 46 of the connector 36 in the embodiment of FIGS. 1-5.

The implementation, arrangement and operation of the connector 62 within the vicinity of the spinal system 10 is substantially identical to the implementation, arrangement and operation of the connector 36 described above in connection with the embodiment of FIGS. 1-5, and therefore will not be described in detail. It is understood that one of the pedicle screws 22, 24, 26, 28, 30 and 32 extends through the slot 64a, and that the planar surface 64c engages one of the vertebrae 12, 14 and 16. It is further understood that each of the planar surfaces 64b and 64c lies in a coronal plane within the vicinity of the spinal system 10.

Figure 7:
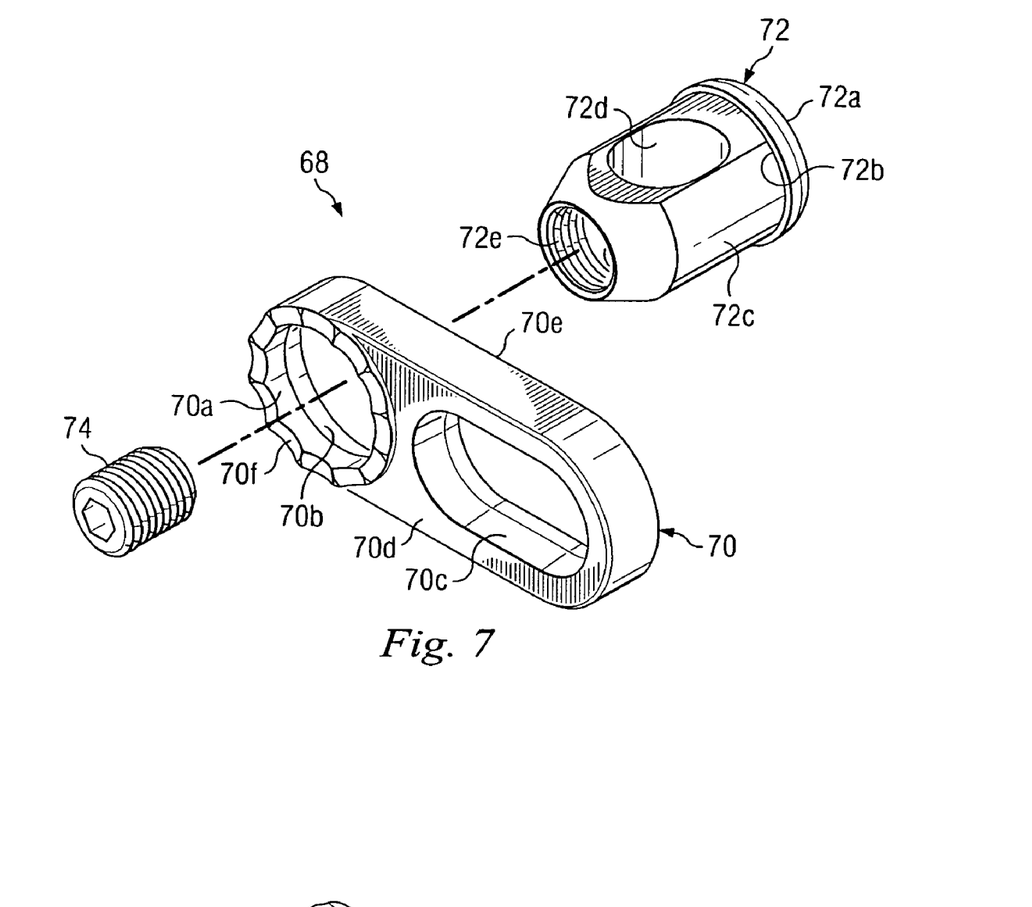
FIG. 7 is an exploded perspective view of a connector according to another embodiment of the present invention.
Figure 8:
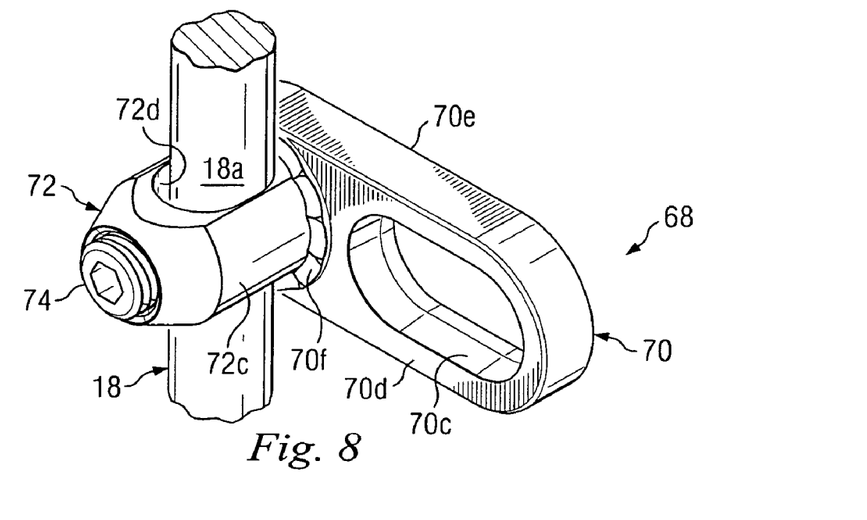
FIG. 8 is an unexploded perspective view of the connector of FIG. 7.

Referring to FIGS. 7 and 8, another embodiment of a connector is generally referred to by the reference numeral 68. A plate member 70 includes a bore 70a defining a tapered surface 70b and an opening such as a slot 70c formed therethrough. The plate member 70 defines a planar surface 70d and a planar surface 70e, the edge of which is shown in FIG. 7. A plurality of partially-circumferentially-extending grooves 70f is formed in the planar surface 70d of the plate member 70, with each groove in the plurality of grooves 70f being adjacent the bore 70a and diametrically opposing one other groove in the plurality of grooves 70f.

A column 72 includes a head portion 72a defining a shoulder 72b, and a cylindrical portion 72c extending from the head portion 72a. A through-opening 72d transversely extends through the cylindrical portion 72c. A bore 72e extends into the through-opening 72d, the bore 72e having an internal threaded connection. The connector 68 further includes a fastener such as a set screw 74.

To place the connector 68 in its assembled condition, as shown in FIG. 8, the cylindrical portion 72c of the column 72 is inserted into the bore 70a of the plate member 70, until the shoulder 72b contacts the tapered surface 70b of the bore 70a. At this point, the column 72 is free to rotate in place, up to 360 degrees and relative to the plate member 70, about an imaginary axis that is substantially coaxial with the center axis of the bore 70a. As the column 72 rotates, the direction of extension of the through-opening 72d is selectively adjusted. Since the center axis of the bore 70a, and therefore the substantially coaxial imaginary axis about which the column 72 rotates, is perpendicular to the planar surfaces 70d and 70e, it is understood that the direction of extension of the through-opening 72d is selectively adjusted in a plane that is either substantially coplanar or parallel with the planar surfaces 70d and/or 70e.

After selectively adjusting the direction of extension of the through-opening 72d, the rod 18 is inserted through the through-opening 72d so that the rod portion 18a is seated in the pair of opposing grooves in the plurality of grooves 70f that corresponds to the direction of extension of the through-opening 72d. Thus, it is understood that by rotating the column 72 to selectively adjust the direction of extension of the through-opening 72d, the direction of extension of the rod portion 18a is also selectively adjusted in a plane that is either substantially coplanar or parallel with the planar surfaces 70d and/or 70e.

The set screw 74 is threadably engaged with the bore 72e so that the set screw 74 extends through the bore 72e and into the through-opening 72d, contacting the rod portion 18a. Further threaded engagement between the set screw 74 and the bore 72e cause the rod portion 18a to bear against the pair of opposing grooves in the plurality of grooves 70f, thereby substantially preventing relative movement between the rod 18 and the column 72.

It is understood that the seating of the rod portion 18a in the pair of opposing grooves in the plurality of grooves 70f locks the direction of extension of the rod portion 18a. It is further understood that the direction of extension of the rod portion 18a may be selectively adjusted and locked in predetermined angular increments, with each predetermined angular increment corresponding to the spacing between adjacent grooves in the plurality of grooves 70f. For example, the center-to-center spacing between adjacent grooves in the plurality of grooves 70f may be 30 degrees. Thus, the direction of extension of the rod portion 18a may be selectively adjusted in 30-degree angular increments.

The implementation, arrangement and operation of the connector 68 within the vicinity of the spinal system 10 is substantially identical to the implementation, arrangement and operation of the connector 36 described above in connection with the embodiment of FIGS. 1-5, and therefore will not be described in detail. It is understood that one of the pedicle screws 22, 24, 26, 28, 30 and 32 extends through the slot 70c, and that the planar surface 70e engages one of the vertebrae 12, 14 and 16. It is further understood that each of the planar surfaces 70d and 70e lies in a coronal plane within the vicinity of the spinal system 10.

Figure 9:
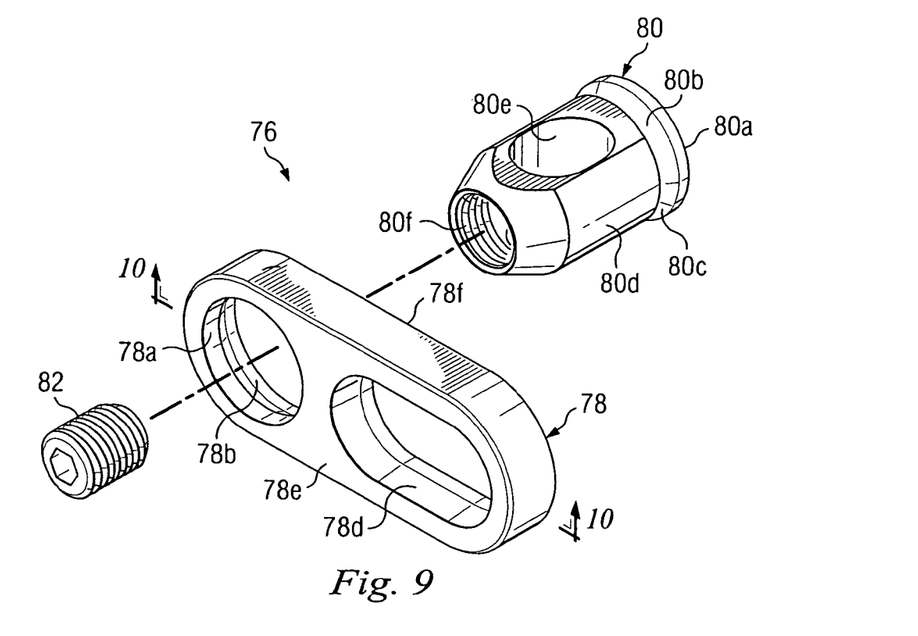
FIG. 9 is an exploded perspective view of a connector according to another embodiment of the present invention.
Figure 10:
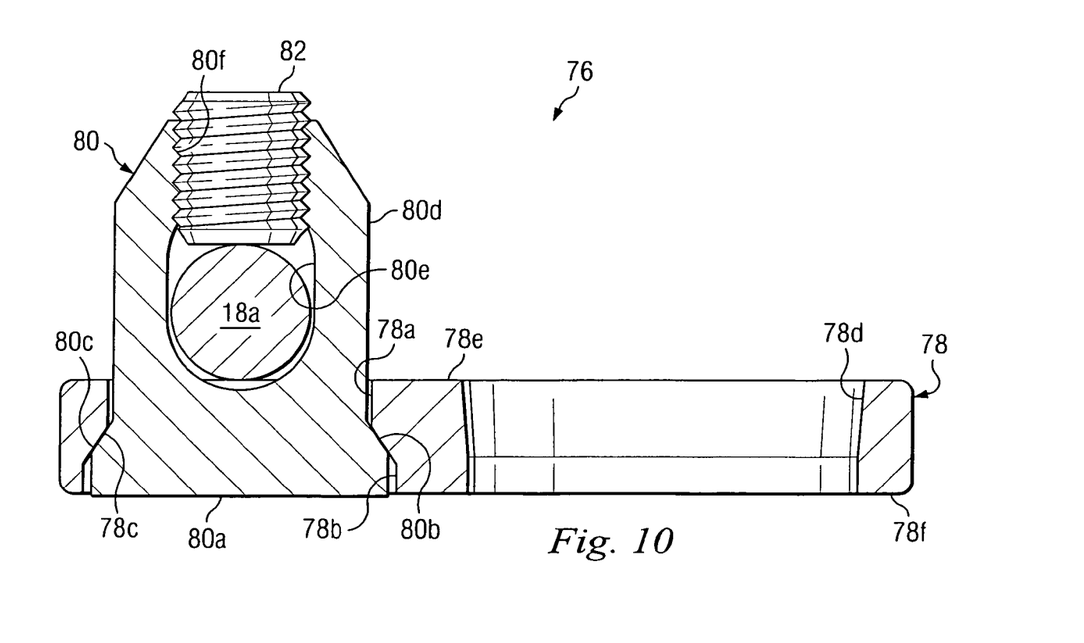
FIG. 10 is an unexploded sectional view of the connector of FIG. 9 taken along line 10-10.

Referring to FIGS. 9 and 10, another embodiment of a connector is generally referred to by the reference numeral 76. A plate member 78 includes a bore 78a having an increased-diameter portion 78b and defining a tapered internal surface 78c. An opening such as a slot 78d is formed through the plate member 78. The plate member 78 defines a planar surface 78e and a planar surface 78f, the edge of which is shown in FIGS. 9 and 10.

A column 80 includes a head portion 80a defining a shoulder 80b which, in turn, defines a tapered external surface 80c. A cylindrical portion 80d extends from the head portion 80a, and a through-opening 80e transversely extends through the cylindrical portion 80d. A bore 80f extends into the through-opening 80e, the bore 80f having an internal threaded connection. The connector 76 further includes a fastener such as a set screw 82.

To place the connector 76 in its assembled condition, as shown in FIG. 10, the cylindrical portion 80d of the column 80 is inserted into the bore 78a of the plate member 78 until the tapered external surface 80c of the column 80 mates with the tapered internal surface 78c defined by the bore 78a of the plate member 78. At this point, the column 80 is free to rotate in place, up to 360 degrees and relative to the plate member 78, about an imaginary axis that is substantially coaxial with the center axis of the bore 78a. As the column 80 rotates, the direction of extension of the through-opening 80e is selectively adjusted. Since the center axis of the bore 78a, and therefore the substantially coaxial imaginary axis about which the column 80 rotates, is perpendicular to the planar surfaces 78e and 78f, it is understood that the direction of extension of the through-opening 80e is selectively adjusted in a plane that is either substantially coplanar or parallel with the planar surfaces 78e and/or 78f.

After selectively adjusting the direction of extension of the through-opening 80e, the rod 18 is inserted through the through-opening 80e so that the rod portion 18a is engaged with the column 80. Thus, it is understood that by rotating the column 80 to selectively adjust the direction of extension of the through-opening 80e, the direction of extension of the rod portion 18a is also selectively adjusted in a plane that is either substantially coplanar or parallel with the planar surfaces 78e and 78f. It is further understood that column 80 may be rotated with the rod portion 18a engaged with the column 80 so that both of the directions of extension of the through-opening 80e and the rod portion 18a are selectively adjusted in a plane that is either substantially coplanar or parallel with the planar surfaces 78e and 78f.

The set screw 82 is threadably engaged with the bore 80f so that the set screw 82 extends through the bore 80f and into the through-opening 80e, contacting the rod portion 18a. Further threaded engagement between the set screw 82 and the bore 80f causes the rod portion 18a to bear against the planar surface 78e, thereby substantially preventing any relative movement between the rod 18 and the column 80.

Further threaded engagement between the set screw 82 and the bore 80f draws the column 80 upward, as shown in FIG. 10, and causes the mating of the external surface 80c of the column 80 and the internal surface 78c of the plate member 78 to form a taper lock between the column 80 and the plate member 78, thereby preventing further rotation of the column 80 relative to the plate member 78. It is understood that the forming of the taper lock between the column 80 and the plate member 78 locks the direction of extension of the rod portion 18a. It is further understood that the direction of extension of the rod portion 18a may be selectively adjusted and locked in an infinite number of angular increments.

The implementation, arrangement and operation of the connector 76 within the vicinity of the spinal system 10 is substantially identical to the implementation, arrangement and operation of the connector 36 described above in connection with the embodiment of FIGS. 1-5, and therefore will not be described in detail. It is understood that one of the pedicle screws 22, 24, 26, 28, 30 and 32 extends through the slot 78d, and that the planar surface 78f engages one of the vertebrae 12, 14 and 16. It is understood that each of the planar surfaces 70e and 70f lies in a coronal plane within the vicinity of the spinal system 10.

An apparatus for stabilizing a spinal system has been described that includes a plate member adapted to be coupled to a vertebra of the spinal system, and means coupled to the plate member for selectively adjusting the direction of extension of at least a portion of a rod in a first coronal plane, wherein the at least a portion of the rod engages the adjusting means when the rod extends within the vicinity of the spinal system.

A method of stabilizing a spinal system has been described that includes engaging a fastener with a vertebra of the spinal system, connecting the fastener to a rod extending within the vicinity of the spinal system, and selectively adjusting the direction of extension of at least a portion of the rod in a first coronal plane.

An apparatus for stabilizing a spinal system has been described that includes a plate member adapted to be coupled to a vertebra of the spinal system, the plate member having an opening formed therethrough wherein a fastener is adapted to extend through the opening to engage the vertebra of the spinal system, and wherein the opening permits the plate member to translate relative to the vertebra and the fastener; means coupled to the plate member for selectively adjusting the direction of extension of at least a portion of a rod in a first coronal plane, wherein the at least a portion of the rod engages the adjusting means when the rod extends within the vicinity of the spinal system, and wherein the adjusting means is able to be rotated in place relative to the plate member to adjust the direction of extension of the at least a portion of the rod in the first coronal plane; and means for locking the direction of extension of the at least a portion of the rod in the first coronal plane.

It is understood that any foregoing spatial references, such as "upper," "lower," "above," "below," "between," "vertical," "angular," "up," "down," "right," "left," etc., are for the purpose of illustration only and do not limit the specific orientation or location of the structure described above.

Moreover, it is understood that any of the above-described connectors 34, 36, 38, 40, 42, 44, 62, 68 and/or 76 may be used in any location, and with any type of vertebra and/or any natural and/or artificial structure extending to or from the vertebra, within the spinal system 10. Further, it is understood that any of the above-described plate members 46, 64, 70 and/or 78 may be rotated relative to any of the rods 18 and/or 20 engaged therewith, and/or relative to any pedicle screw 22, 24, 26, 28, 30 and/or 32 engaged therewith. Still further, it is understood that conventional stabilizer components may be disposed in channels formed in one or more of the above-described plate members 46, 64, 70 and/or 78 so that any of the pedicle screws 22, 24, 26, 28, 30 and/or 32 engaged with any of the plate members 46, 64, 70 and/or 78 also extend through the stabilizer component. It is further understood that the cross-sections of the rods 18 and/or 20 extending within the vicinity of the spinal system 10 may be varied, and that the corresponding cross-sections of the through-openings 50b, 72d and/or 80e through which the rods 18 and/or 20 extend may also be correspondingly varied.

Also, it is understood that each of the above-described embodiments may be combined in whole or in part with one or more of the other above-described embodiments. It is further understood that each of the above-described embodiments may be combined in whole or in part with other components, devices, systems, methods and/or surgical techniques known to those skilled in the art to provide spinal stabilization.

Although exemplary embodiments of this invention have been described in detail above, those skilled in the art will readily appreciate that many other modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents, but also equivalent structures.

What is claimed is:

1. An apparatus for stabilizing a spinal system, the apparatus comprising:
   a plate member adapted to be coupled to a vertebra of the spinal system;
   an adjusting means coupled to the plate member for selectively adjusting the direction of extension of at least a portion of a rod in a first coronal plane; and
   a washer disposed between the adjusting means and the plate member, the washer comprising a first plurality of teeth for engaging the plate member at a plurality of predetermined angular increments;
   wherein the at least a portion of the rod engages the adjusting means;
   wherein the adjusting means is able to be rotated in place relative to the plate member to adjust the direction of extension of the at least a portion of the rod in the first coronal plane;
   wherein the adjusting means comprises a housing member comprising:
      a collar portion having a through-opening through which the at least a portion of the rod is adapted to extend; and
      a coupling means extending from the collar portion for coupling the housing member to the plate member;
   wherein the coupling means comprises a pair of arms extending from the collar portion and through a bore formed through the plate member to form a snap fit between the housing member and the plate member; and
   wherein the adjusting means further comprises a clip member disposed between the arms and engaged with the plate member to prevent the housing member from decoupling from the plate member.

2. The apparatus of claim 1 wherein the clip member comprises a pair of legs wherein each leg engages the plate member and is biased in a direction away from the other leg when the clip member is disposed between the arms of the housing member.

3. An apparatus comprising:
   a plate member having a first portion and a second portion, the first portion having a first opening and a first plurality of teeth at least partially surrounding the first opening, and the second portion having a second opening, the second opening being elongated;
   a coupling element comprising:
      a first rod-receiving aperture extending through the coupling element along a first axis;
      a second aperture extending through the coupling element along a second axis, the second axis being substantially perpendicular to the first axis;
      a pair of arms for snap-fit engagement with the first opening of the first portion of the plate member, the pair of arms extending substantially parallel to the second axis;
   a spacer disposed between the coupling element and the plate member having a second plurality of teeth for engagement with the first plurality of teeth in a plurality of predetermined angular increments; and
   a clip for positioning between the pair of arms to retain engagement between the coupling element and the plate member wherein the clip is configured to snap-fit with the first opening of the first portion of the plate member.

4. The apparatus of claim 3 wherein the coupling element and the spacer can rotate 360 degrees about the second axis relative to the plate member.

5. The apparatus of claim 3 wherein the spacer further comprises an indentation for receiving a portion of the coupling element.

6. The apparatus of claim 3 wherein the spacer further comprises a rod receiving profile.

7. The apparatus of claim 6 further comprising a fastener to secure a rod within the first rod-receiving aperture of the coupling element and in engagement with the rod receiving profile of the spacer.

8. The apparatus of claim 7, wherein the fastener further secures the spacer with respect to the plate member at one of the plurality of predetermined angular increments for engagement between the first plurality of teeth and the second plurality of teeth.

9. An apparatus comprising:
   a plate member having a first portion and a second portion, the first portion having a first opening and a first plurality of teeth at least partially surrounding the first opening, and the second portion having a second opening;
   a coupling element comprising:
      a first rod-receiving aperture extending through the coupling element along a first axis;
      a second aperture extending through the coupling element along a second axis, the second axis being substantially perpendicular to the first axis;
      a pair of arms in snap-fit engagement with the first opening of the first portion of the plate member, the pair of arms extending substantially parallel to the second axis;
   a spacer disposed between the coupling element and the plate member having a second plurality of teeth engaging the first plurality of teeth of the plate member, the second plurality of teeth engageable with the first plurality of teeth in a plurality of predetermined angular increments; and
   a locking member positioned between the pair of arms to retain the snap-fit engagement between the pair of arms of the coupling element and the plate member, the locking member engaging both the coupling element and the plate member.

10. The apparatus of claim 9 wherein the spacer is sized and shaped to rotate with respect to the plate member about the second axis.

11. The apparatus of claim 10 wherein the spacer is sized and shaped to rotate with respect to the plate member about the second axis in the plurality of predetermined angular increments.

12. The apparatus of claim 10 wherein the spacer is able to rotate about the second axis 360 degrees.

13. The apparatus of claim 10 further comprising a fastener extending through the second opening to engage a bone structure.

14. The apparatus of claim 13 wherein the second opening is elongated to permit translation of the plate member relative to the fastener.

15. The apparatus of claim 9 wherein the first portion of the plate member extends generally in a first plane and wherein the second portion of the plate member extends generally in a second plane offset from the first plane.

16. The apparatus of claim 15, wherein the second plane extends substantially parallel to the first plane such that the second portion extends substantially parallel to the first portion.

17. The apparatus of claim 9 wherein the spacer is positioned adjacent the first rod receiving aperture such that, when a rod is secured within the first rod-receiving aperture, at least a portion of the rod bears against the spacer.

18. The apparatus of claim 17 further comprising a securing member engaged with the second aperture to secure the rod within the first rod-receiving aperture.

19. The apparatus of claim 18 wherein the securing member is threadably engaged with a threaded portion of the second aperture, the securing member extending within the second aperture to contact the rod such that the at least a portion of the rod bears against the spacer.

* * * * *

UNITED STATES PATENT AND TRADEMARK OFFICE
CERTIFICATE OF CORRECTION

PATENT NO.      : 7,585,312 B2
APPLICATION NO. : 11/118995
DATED           : September 8, 2009
INVENTOR(S)     : Rawlins et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 697 days.

Signed and Sealed this

Fourteenth Day of September, 2010

David J. Kappos
*Director of the United States Patent and Trademark Office*